United States Patent [19]

Takacs et al.

[11] 4,308,270
[45] Dec. 29, 1981

[54] 1,2,4-OXADIAZINE DERIVATIVES, PROCESS FOR THEIR PREPARATION AND PHARMACEUTICAL COMPOSITIONS CONTAINING THEM

[75] Inventors: Kálmán Takacs; Antal Simay; Ilona Kiss nee Ajzert; Péter L. Nagy; Maria Hetyey nee Papp; Marian Ecsery nee Puskas; József Szegy; Sándor Viragh; Sandor J. Nagy, all of Budapest, Hungary

[73] Assignee: Chinoin Gyogyszer es Vegyeszeti Termekek Gyara Rt, Budapest, Hungary

[21] Appl. No.: 196,034

[22] Filed: Oct. 10, 1980

[30] Foreign Application Priority Data

Oct. 11, 1979 [HU] Hungary .............................. CI 1974

[51] Int. Cl.³ .................. A61K 31/535; C07D 273/04
[52] U.S. Cl. .................................. 424/248.56; 544/66
[58] Field of Search ...................... 544/66; 424/248.56

[56] References Cited

U.S. PATENT DOCUMENTS 4,154,598  5/1979  Farge et al. .......................... 544/66

OTHER PUBLICATIONS

Takacs et al., "Chem. Berichte", (1975), vol. 108, No. 6, pp. 1911–1923.

Primary Examiner—Robert T. Bond
Attorney, Agent, or Firm—Karl F. Ross

[57] ABSTRACT

The invention concerns new compounds of the general formula (I)

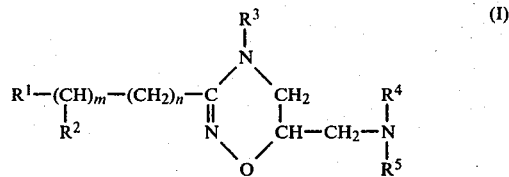

wherein
$R^1$ is hydrogen or phenyl optionally substituted by one or more of the following substituents: alkyl having 1 to 4 carbon atoms, halogen, alkoxy having 1 to 4 carbon atoms or nitro;
$R^2$ is alkyl having 1 to 4 carbon atoms, cycloalkyl having 5 to 7 carbon atoms or phenyl, optionally substituted with one or more of the following groups: alkyl having 1 to 4 carbon atoms, halogen, alkoxy having 1 to 4 carbon atoms or nitro; or $R^2$ is a naphthyl group;
$R^3$ is alkyl having 1 to 4 carbon atoms, acyl or hydrogen;
$R^4$ hydrogen or alkyl having 1 to 4 carbon atoms;
$R^5$ is cycloalkyl having 5 to 7 carbon atoms, alkyl having 1 to 6 carbon atoms, phenyl-($C_{1-4}$-alkyl) in which the phenyl moiety may optionally be substituted with alkoxy having 1 to 4 carbon atoms, halogen or nitro;
or $R^4$ and $R^5$ together represent a group of the general formula (V)

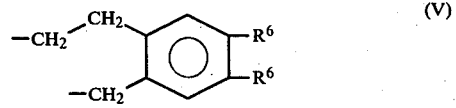

wherein
$R^6$ is hydrogen or alkoxy having 1 to 4 carbon atoms, m and n stand for 0, 1 or 2
and acid addition and quaternary salts thereof.

The compounds of the general formula (I) are potent peripheral vasodilators and hypotensive agents. They increase the coronary blood flow and in addition to their slight antiinflammatory and diuretic acidivity possess strong antiarrhythmic properties.

A process for the preparation of these compounds and pharmaceutical compositions containing them are also within the scope of the invention.

19 Claims, No Drawings

1,2,4-OXADIAZINE DERIVATIVES, PROCESS FOR THEIR PREPARATION AND PHARMACEUTICAL COMPOSITIONS CONTAINING THEM

The invention relates to new 1,2,4-oxadiazine derivatives, a process for the preparation thereof and pharmaceutical compositions containing them. More particularly, the invention concerns new 1,2,4-oxadiazine derivatives of the formula (I)

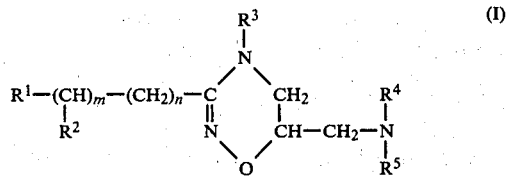

wherein
- $R^1$ is hydrogen or phenyl optionally substituted by one or more of the following substituents: alkyl having 1 to 4 carbon atoms, halogen, alkoxy having 1 to 4 carbon atoms or nitro;
- $R^2$ is alkyl having 1 to 4 carbon atoms, cycloalkyl having 5 to 7 carbon atoms or phenyl, optionally substituted with one or more of the following groups: alkyl having 1 to 4 carbon atoms, halogen, alkoxy having 1 to 4 carbon atoms or nitro; or $R^2$ is a naphthyl group;
- $R^3$ is alkyl having 1 to 4 carbon atoms, acyl or hydrogen;
- $R^4$ is hydrogen or alkyl having 1 to 4 carbon atoms;
- $R^5$ is cycloalkyl having 5 to 7 carbon atoms, alkyl having 1 to 6 carbon atoms, phenyl-($C_{1-4}$-alkyl) in which the phenyl moiety may optionally be substituted with alkoxy having 1 to 4 carbon atoms, halogen or nitro;
- or $R^4$ and $R^5$ together are a group of the formula (V)

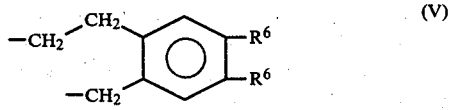

wherein
$R^6$ is hydrogen or alkoxy having 1 to 4 carbon atoms, m and n stand for 0, 1 or 2.

Throughout the specification the following further symbols are used:
Z is halogen or sulfonyoxy;
X,Y is halogen;
$R^7$ is hydrogen or an alkyl having 1 to 4 carbon atoms;
Q is 3-chloro-2-hydroxypropyl or 2,3-epoxypropyl group.

The term "acyl" in the definition or $R^3$ preferably refers to benzoyl, which may optionally be substituted with an alkyl having 1 to 4 carbon atoms, alkoxy having 1 to 4 carbon atoms, nitro or halogen. Further preferred representatives of acyl groups are tosyl and alkanoyl having 1 to 4 carbon atoms.

The term "alkyl" alone or in alkyl-containing groups is used to refer to straight or branched chained hydrocarbon groups.

According to the invention compounds of the formula (I), wherein $R^1$, $R^2$, $R^3$, $R^4$, $R^5$, $R^6$, m and n are as hereinabove defined, are prepared by (a) reacting a compound of the formula (II)

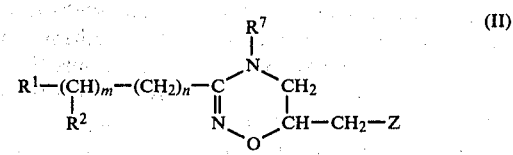

with a compound of the formula (III)

to give compounds of the formula (I), in which $R^7$ is alkyl having 1 to 4 carbon atoms or hydrogen; or (b) reacting a new compound of the formula (IV)

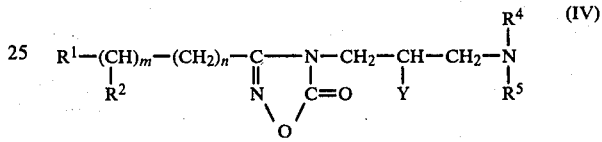

with a base to prepare compounds of the formula (I), in which $R^3$ is hydrogen; or (c) acylating a compound of the formula (I), in which $R^3$ is hydrogen in a manner known per se, to prepare compounds of the formula (I), in which $R^3$ is an acyl group; or (d) hydrolyzing compounds of the formula (I), in which $R^3$ is acyl in a manner known per se, to prepare compounds of the formula (I), in which $R^3$ is hydrogen.

Compounds of the formula (I) are potent peripheral vasodilators and hypotensive agents. They increase the coronary blood flow, and in addition to their slight antiinflammatory and diuretic activity possess a strong antiarrhythmic activity as well.

Closely related oxadiazine derivatives, which contain a nitrofuryl or an 5-imino substituent are disclosed in C.A. 75, 20450 (1971) and J. Heterocycl. Chem. 9, 435 (1972), respectively. These compounds are reported to have antibacterial activity.

According to a preferred embodiment of process variant (a) the reaction is carried out in melt, or by heating in organic solvents, preferably at a temperature of 80° to 180° C. As a solvent an excess amount of the secondary amine of the formula (III) can also be used. Further suitable organic solvents include aromatic hydrocarbons, such as benzene, toluene, chlorobenzene, dichlorobenzene, etc. As an acid binding agent an excess of secondary amine or alkali hydroxides, carbonates, hydrocarbonates, etc. can be employed.

The compounds of the formula (I) can be isolated by known techniques, such as crystallization, extraction, etc. If desired, acid addition salts and quaternary salts can also be prepared.

The starting compounds of the formula (II) can be prepared by halogenating or acylating the corresponding 6-hydroxymethyl-1,2,4-oxadiazine derivatives. For the acylation sulfonic acid halides can be used. [Chem. Ber. 108, 1911 (1975)].

Process variant (b) according to the invention is preferably carried out in an aqueous alkali hydroxide solution, at the boiling temperature of the reaction mixture. To increase the solubility of the starting compounds of the formula (IV) the reaction can also be carried out in a mixture of aqueous solutions of alkali hydroxides and water-miscible organic solvents, such as ethanol, methanol, dioxane, etc. Compounds of the formula (I) can be isolated by techniques known per se, e.g. by crystallization, extraction, etc. If desired, the compounds of the formula (I) can be converted into their quaternary or acid addition salts. The starting compounds of the formula (IV) are new can be prepared from the new compounds of the formula (VI)

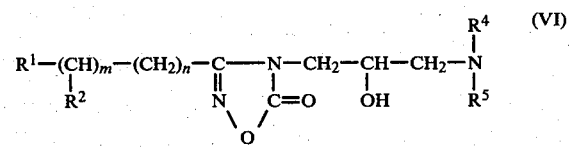

by means of halogenating agents, such as thionyl chloride, phosphorus pentachloride, etc. in a known manner. On the other hand, compounds of the formula (VI) can be prepared following the procedure described in Chem. Ber. 108, 1911 (1975), for example by reacting compounds of the formula (VII)

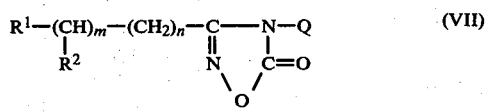

with compounds of the formula (III).

Process variant (c) according to the invention is preferably carried out in organic solvents. As acylating agents acid halides, acid anhydrides or acid azides can be used.

The invention relates also to pharmaceutical compositions containing compounds of the formula (I) or pharmaceutically acceptable salts thereof in admixture with non-toxic, pharmaceutically acceptable organic and/or inorganic carriers and optionally other additives. The pharmaceutical compositions can be prepared as various formulations, including solid formulations, such as tablets, dragees, etc. and liquid formulations, such as solutions or emulsions. The pharmaceutical compositions are prepared by known techniques of the pharmaceutical industry.

EXAMPLE 1

To 5.0 g. of 3-phenyl-6-chloromethyl-5,6-dihydro-4H-1,2,4-oxadiazine (Chem. Ber. 108, 1911 (1975) 37 ml. of cyclohexyl amine are added. The reaction mixture is then refluxed for 10 hours. The excess of cyclohexyl amine is evaporated in vacuo and to the evaporation residue 100 ml. of ethyl acetate are added. The mixture is brought to the boil and the insoluble substances are filtered off while hot. The mother liquor is evaporated in vacuo, the residue is dissolved in isopropanol and the solution is acidified by introducing hydrogen chloride gas. 4.0 g. of 3-phenyl-6-cyclohexylaminomethyl-5,6-dihydro-4H-1,2,4-oxadiazine dihydrochloride are obtained, melting at 240° to 244° C. (after recrystallization from isopropanol).

Analysis for $C_{16}H_{25}N_3OCl_2$: calculated: C=55.49%; H=7.28%; N=12.14%; Cl=20.48%; found: C=55.27%; H=7.40%; N=12.04%; Cl=20.25%.

$LD_{50}$: 51 mg./kg. i.v. on mice. 10 minutes after the administration of a 2.5 mg./kg. i.v. dose of the compound a 20% reduction of blood pressure of anaesthetized cats has been observed. On dogs a 10 mg./kg. i.v. dose results in a 15% reduction in the peripheral resistance. In dextrate oedema test on rats a 5.1 mg./kg. dose provides a 15% protecting effect.

EXAMPLE 2

Following the procedure described in Example 1 but starting from 3-phenyl-6-chloromethyl-5,6-dihydro-4H-1,2,4-oxadiazine and methyl-cyclohexyl amine, 3-phenyl-6-(N-methyl-N-cyclohexylamino)-methyl-5,6-dihydro-4H-1,2,4-oxadiazine dihydrochloride is obtained, melting at 243° to 246° C. (after recrystallization from absolute alcohol).

Analysis for $C_{17}H_{27}N_3OCl_2$: calculated: C=56.66%; N=7.55%; N=11.66%; Cl=19.68%; found: C=57.07%; N=7.91%; N=11.35%; Cl=20.09%.

EXAMPLE 3

To 2.0 g. of 3-phenyl-6-tosyloxymethyl-5,6-dihydro-4H-1,2,4-oxadiazine 30 ml. of chlorobenzene and 3 ml. of methylcyclohexyl amine are added and the reaction mixture is refluxed for 6 hours. The mixture is then cooled down and the precipitated product is filtered off, dissolved in ethyl acetate and the solution is acidified with hydrochloric acid in ethanol. 1.1 g. of 3-phenyl-6-(N-methyl-N-cyclohexylamino)-methyl-5,6-dihydro-4H-1,2,4-oxadiazine dihydrochloride are obtained, which has the same properties as the product of Example 2.

EXAMPLE 4

To 50.6 g. of 3-phenyl-4-[3-(1,2,3,4-tetrahydro-2-isoquinolyl)-2-chloropropyl]-Δ$^2$-1,2,4-oxadiazolin-5-one hydrochloride 300 ml. of a 96% ethanol and 300 ml. of a 10% sodium hydroxide solution are added, the reaction mixture is refluxed for one and a half hours, and the ethanol is evaporated in vacuo. Upon cooling 33.9 g. of crystalline 3-phenyl-6-(1,2,3,4-tetrahydro-2-isoquinolyl)-methyl-5,6-dihydro-4H-1,2,4-oxadiazine are obtained, melting at 187° to 189° C. after recrystallization from absolute ethanol.

Analysis for $C_{19}H_{21}N_3O$: calculated: C=17.24%; H=6.89%; N=13.67%; found: C=74.50%, H=7.06%; N=13.59%.

The hydrochloride of the product is precipitated from a solution in isopropanol by introducing hydrogen chloride gas. The hydrochloride melts at 240° C.

Analysis for $C_{19}H_{23}N_3OCl_2$: calculated: Cl=18.65%; found: Cl=18.95%.

$LD_{50}$: 332 mg./kg. p.o. on mice; 52.8 mg./kg. i.v. on mice.

A 10 mg./kg. dose of the compound increases the blood flow in the femoral artery of dogs to 181%. 2 minutes after administration. The obtained increase corresponds to 246% local conductivity (control: 100%). Under the same conditions the blood pressure is reduced to 72% of its original value, the cardiac output is increased to 125%, and the coronary blood flow is increased to 127%. 4 mg./kg. i.p. dose of the compound results in a 59% increase in the quantity of the discharged urine on rats, related to the control. A 4 mg./kg. i.v. dose shows a 35% protecting activity in dextrane oedema test carried out on rats.

EXAMPLE 5

10.5 g. of 3-phenyl-6-chloromethyl-5,6-dihydro-4H-1,2,4-oxadiazine 6.7 g. of 1,2,3,4-tetrahydro-isoquinoline, 6.9 g. of anhydrous potassium carbonate and 80 ml. of chlorobenzene are added. The reaction mixture is refluxed for 6 hours. The solution is filtered while hot and cooled to room temperature. 6.5 g. of 3-phenyl-6-(1,2,3,4-tetrahydro-2-isoquinolyl)-methyl-5,6-dihydro-4H-1,2,4-oxadiazine are obtaned in crystalline form. The product has the same properties as the product of Example 4. Melting point: 187° to 189° C.

EXAMPLE 6

To 3.46 g. of 3-phenyl-6-tosyloxymethyl-5,6-dihydro-4H-1,2,4-oxadiazine 1.33 g. of 1,2,3,4-tetrahydro-isoquinoline, 1.38 g. of anhydrous potassium carbonate and 30 ml. of chlorobenzene are added. The reaction mixture is refluxed for 2 hours, whereupon it is decolored and filtered while hot. Upon cooling 1.95 g. of 3-phenyl-6-(1,2,3,4-tetrahydro-2-isoquinolyl)-methyl-5,6-dihydro-4H-1,2,4-oxadiazine are obtained in crystalline form. The product has the same properties as the product of Example 4. Melting point: 187° to 189° C.

EXAMPLE 7

Following the procedure described in Example 6 but replacing chlorobenzene by 60 ml. of butanol, 1.88 g. of 3-phenyl-6-(1,2,3,4-tetrahydro-2-isoquinolyl)-methyl-5,6-dihydro-4H-1,2,4-oxadiazine are obtained, having the same properties as the product of Example 4. Melting point: 187° to 189° C.

EXAMPLE 8

Following the procedure described in Example 6 but starting from 2.7 g of 3-phenyl-6-mesyloxymethyl-5,6-dihydro-4H-1,2,4-oxadiazine and 1,2,3,4-tetrahydro-isoquinoline, 1.86 g. of 3-phenyl-6-(1,2,3,4-tetrahydro-2-isoquinolyl)-methyl-5,6-dihydro-4H-1,2,4-oxadiazine are obtained, having the same properties as the product of Example 4. Melting point: 187° to 189° C.

EXAMPLE 9

Following the procedure described in Example 5 but starting from 3-phenyl-6-chloromethyl-5,6-dihydro-4H-1,2,4-oxadiazine and 6,7-dimethoxy-1,2,3,4-tetrahydro-isoquinoline, 3-phenyl-6-(6,7-dimethoxy-1,2,3,4-tetrahydro-2-isoquinolyl)-methyl-5,6-dihydro-4H-1,2,4-oxadiazine is obtained, melting at 162° to 163° C. (after recrystallization from absolute ethanol).

Analysis for $C_{21}H_{25}N_3O_3$: calculated: C=68.64%; H=6.86%; N=11.44%; found: C=68.48%; H=7.20%; N=11.85%.

The hydrogen maleate of the product is precipitated from a solution in absolute ethanol by maleic acid. The salt melts at 177° C.

Analysis for $C_{25}H_{29}N_3O_7$: calculated: C=62.10%; H=6.05%; N=8.69%; found: C=61.86%; H=5.97%; N=8.62%.

$LD_{50}$: 148 mg./kg. i.v. on mice. A 10 mg./kg. i.v. dose induces a lasting reduction of blood pressure of anaesthetized cats.

EXAMPLE 10

Following the procedure described in Example 5 but starting from 3-(2-chlorophenyl)-6-chloromethyl-5,6-dihydro-4H,1,2,4-oxadiazine and 1,2,3,4-tetrahydro-isoquinoline, 3-(2-chlorophenyl)-6-(1,2,3,4-tetrahydro-2-isoquinolyl)-methyl-5,6-dihydro-4H,1,2,4-oxadiazine is obtained, melting at 147° to 150° C. after recrystallization from ethyl acetate.

Analysis for $C_{19}H_{20}N_3OCl$: calculated: C=66.76%; H=5.90%; N=12.29%; Cl=10.37%; found: C=66.38%; H=5.83%; N=12.00%; Cl=10.69%.

The dihydrochloride of the product is precipitated by introducing hydrochloric acid gas into an isopropanolic solution thereof. The salt melts at 227° to 230° C.

Analysis for $C_{19}H_{22}N_3OCl_3$: calculated: Cl=25.65%; found: Cl=25.42%.

EXAMPLE 11

Following the procedure described in Example 5 but starting from 3-(4-chlorophenyl)-6-chloromethyl-5,6-dihydro-4H,1,2,4-oxadiazine and 1,2,3,4-tetrahydro-isoquinoline, 3-(4-chlorophenyl)-6-(1,2,3,4-tetrahydro-2-isoquinolyl)-methyl-5,6-dihydro-4H-1,2,4-oxadiazine hemihydrate is obtained, melting at 190° to 192° C. after recrystallization from a 96% ethanol.

Analysis for $C_{19}H_{20}N_3OCl.0.5\ H_2O$: calculated: C=65.04%; H6.03%; N=11.98%; Cl=10.11%; found: C=65.48%; H=6.20%; N=11.84%; Cl=10.50%;

The dihydrochloride of the product is precipitated by introducing hydrogen chloride gas into an isopropanolic solution thereof. The salt melts at 249° to 252° C.

Analysis for $C_{19}H_{22}N_3OCl_3$: calculated: Cl=25.65%; found: Cl=25.32%.

EXAMPLE 12

To 4.21 g. of 3-(4-chlorophenyl)-4-[3-(1,2,3,4-tetrahydro-2-isoquinolyl)-2-chloropropyl]-$\Delta^2$-1,2,4-oxadiazolin-5-one hydrochloride 30 ml. of ethanol and 20 ml. of 10% sodium hydroxide are added. The reaction mixture is then refluxed for one and a half hour. The alcohol is evaporated in vacuo. 3.0 g. of 3-(4-chlorophenyl)-6-(1,2,3,4-tetrahydro-2-isoquinolyl)-methyl-5,6-dihydro-4H-1,2,4-oxadiazine hemihydrate are obtained, having the same properties as the product of Example 11. Melting point: 190° C.

EXAMPLE 13

To 5.94 g. of 3-(4-tolyl)-6-chloromethyl-5,6-dihydro-4H-1,2,4-oxadiazine 5.32 g. of 1,2,3,4-tetrahydro-isoquinoline, 5.52 g. of anhydrous potassium carbonate and 40 ml. of absolute xylene are added. The reaction mixture is then refluxed for 8 hours. The insoluble substances are filtered off while hot. The filtrate is cooled to room temperature and the crystalline precipitate obtained is filtered off and dried. The product is then dissolved in isopropanol and hydrogen chloride gas is introduced to yield 4.1 g. of 3-(4-tolyl)-6-(1,2,3,4-tetrahydro-2-isoquinolyl)-methyl-5,6-dihydro-4H-1,2,4-oxadiazine dihydrochloride, melting at 250° C.

Analysis for $C_{20}H_{25}N_3OCl_2$: calculated: Cl=17.98%; found: Cl=18.44%.

EXAMPLE 14

Following the procedure described in Example 4 but starting from 4.5 g. of 3-benzyl-4-[3-(1,2,3,4-tetrahydro-2-isoquinolyl)-chloropropyl]-$\Delta^2$-1,2,4-oxadiazolin-5-one hydrochloride, 2.4 g. of 3-benzyl-6-(1,2,3,4-tetrahydro-2-isoquinolyl)-methyl-5,6-dihydro-4H-1,2,4-oxadiazine are obtained, melting at 146° to 148° C., after recrystallization from isopropanol.

Analysis for $C_{20}H_{23}N_3O$: calculated: $C=74.73\%$; $H=7.21\%$; $N=13.07\%$; found: $C=74.35\%$; $H=7.06\%$; $N=12.68\%$.

EXAMPLE 15

Following the procedure described in Example 1 but starting from 3-(2,2-dimethylethyl)-6-chloromethyl-5,6-dihydro-4H-1,2,4-oxadiazine and cyclohexyl amine, 3-(2,2-diphenylethyl)-6-cyclohexylaminomethyl-5,6-dihydro-1,2,4-oxadiazine dihydrochloride is obtained, melting at 252° to 255° C.

Analysis for $C_{24}H_{33}N_3OCl_2$: calculated: $C=63.99\%$; $H=7.38\%$; $N=9.33\%$; $Cl=15.74\%$; found: $C=64.15\%$; $H=7.49\%$; $N=9.28\%$; $Cl=15.66\%$.

$LD_{50}=16.0$ mg./kg. iv. on mice.

EXAMPLE 16

Following the procedure described in Example 1 but starting from 3-(2,2-diphenylethyl)-6-chloromethyl-5,6-dihydro-4H-1,2,4-oxadiazine and methylcyclohexyl amine, 3-(2,2-diphenylethyl)-6-(N-methyl-N-cyclohexylamino)-methyl-5,6-dihydro-4H-1,2,4-oxadiazine dihydrochloride is obtained, melting at 227° to 230° C.

Analysis for $C_{25}H_{35}N_3OCl_2$: calculated: $C=64.64\%$; $H=7.60\%$; $N=9.05\%$; $Cl=15.27\%$; found: $C=65.01\%$; $H=7.75\%$; $N=9.14\%$; $Cl=14.94\%$.

$LD_{50}$: 160.0 mg./kg. i.v. on mice. By a 1 mg./kg. i.v. dose of the compound the blood flow in the femoral artery of anaesthetized dogs is increased by 70%, 5 minutes after administration. The same dose reduces the blood pressure of anaesthetized cats by 20%. In dextrane oedema test carried out on rats 16 mg./kg. dose of the compound provides a 55% protection. Administration of a 16 mg./kg. i.p. dose to mice in four hours increases the urinary output to 160% related to the untreated control (100%).

EXAMPLE 17

Following the procedure described in Example 4 but starting from 23.0 g. of 3-(2,2-diphenylethyl)-4-[3-(1,2,3,4-tetrahydro-2-isoquinolyl)-2-chloropropyl]-$\Delta^2$-1,2,4-oxadiazolin-5-one hydrochloride, 15.4 g. of 3-(2,2-diphenylethyl)-6-(1,2,3,4-tetrahydro-2-isoquinolyl)-methyl-5,6-dihydro-4H-1,2,4-oxadiazine are obtained, melting at 163° C., after recrystallization from absolute ethanol.

Analysis for $C_{27}H_{29}N_3O$: calculated: $C=78.80\%$; $H=7.10\%$; $N=10.21\%$; found: $C=78.95\%$; $H=7.15\%$; $N=10.46\%$.

The dihydrochloride of the product is precipitated by introducing hydrogen chloride gas into an isopropanolic solution thereof. The salt melts at 240° to 245° C.

Analysis for $C_{27}H_{31}N_3OCl_2$: calculated: $C=66.93\%$; $H=6.45\%$; $N=8.67\%$; $Cl=14.64\%$; found: $C=66.54\%$; $H=6.05\%$; $N=8.37\%$; $Cl=14.20\%$.

$LD_{50}=72.0$ mg./kg. i.v. on mice. A 3.6 mg./kg. i.v. dose of the compound reduces the blood pressure of anaesthetized cats by 20%.

EXAMPLE 18

To 1.2 g. of 3-(2,2-diphenylethyl)-6-mesyloxymethyl-5,6-dihydro-4H-1,2,4-oxadiazine 1.0 ml. of 1,2,3,4-tetrahydro-isoquinoline and 15 ml. of chlorobenzene are added. The reaction mixture is refluxed for 10 hours. The solvent is evaporated in vacuo and to the residue ethyl acetate is added. 0.6 g. of 3-(2,2-diphenylethyl)-6-(1,2,3,4-tetrahydro-2-isoquinolyl)-methyl-5,6-dihydro-4H-1,2,4-oxadiazine are added, having the same properties as the product of Example 17. Melting point: 163° C.

EXAMPLE 19

Following the procedure described in Example 18 but starting from 2.0 g. of 3-(2,2-diphenylethyl)-6-tosyloxymethyl-5,6-dihydro-4H-1,2,4-oxadiazine, 1.0 g. of 3-(2,2-diphenylethyl)-6-(1,2,3,4-tetrahydro-2-isoquinolyl)-methyl-5,6-dihydro-4H-1,2,4-oxadiazine are obtained, having the same properties as the product obtained in Example 17. Melting point: 163° C.

EXAMPLE 20

To 3.08 g. of 3-phenyl-6-(1,2,3,4-tetrahydro-2-isoquinolyl)-methyl-5,6-dihydro-4H-1,2,4-oxadiazine 50 ml. of absolute acetone, 1.0 ml. of chlorocarbonic acid ethyl ester and 1.0 g. of anhydrous potassium carbonate are added. The reaction mixture is refluxed for 6 hours. The insoluble substances are filtered off while hot and the solvent is evaporated. After recrystallization of the residue from cyclohexane 1.18 g. of 3-phenyl-4-ethoxycarbonyl-6-(1,2,3,4-tetrahydro-2-isoquinolyl)-methyl-5,6-dihydro-1,2,4-oxadiazine are obtained, melting at 114° to 116° C.

Analysis for $C_{22}H_{25}N_3O_3$: calculated: $C=69.63\%$; $H=6.64\%$; $N=11.08\%$; found: $C=69.87\%$; $H=6.25\%$; $N=11.30\%$.

The maleate of the above compound is precipitated from its acetonic solution by adding maleic acid. Melting point: 165° to 168° C., after recrystallization from isopropanol.

Analysis for $C_{26}H_{29}N_3O_2$: calculated: $C=63.02\%$; $H=5.90\%$; $N=8.48\%$; found: $C=63.45\%$; $H=6.24\%$; $N=8.25\%$.

EXAMPLE 21

Following the procedure described in Example 20 but starting from 3-phenyl-6-(1,2,3,4-tetrahydro-2-isoquinolyl)-methyl-5,6-dihydro-4H-1,2,4-oxadiazine and benzoyl chloride, 3-phenyl-4-benzoyl-6-(1,2,3,4-tetrahydro-2-isoquinolyl)-methyl-5,6-dihydro-1,2,4-oxadiazine is obtained, melting at 174° to 175° C., after recrystallization from isopropanol.

Analysis for $C_{26}H_{25}N_3O_2$: calculated: $C=75.89\%$; $H=6.12\%$; $N=10.21\%$; found: $C=75.80\%$; $H=6.13\%$; $N=9.98\%$.

EXAMPLE 22

To 2.0 g. of 3-phenyl-6-(1,2,3,4-tetrahydro-2-isoquinolyl)-methyl-5,6-dihydro-4H-1,2,4-oxadiazine 1.0 g. of anhydrous potassium carbonate, 5.0 ml. of methyl iodide and 80 ml. of absolute acetone are added. The reaction mixture is then refluxed for 3 hours. The insoluble part is filtered off while hot, the filtrate is evaporated. After recrystallization of the residue from a 96% ethanol, 1.45 g. of 3-phenyl-4-methyl-6-(1,2,3,4-tetrahydro-2-isoquinoline)-methyl-5,6-dihydro-1,2,4-oxadiazine diiodomethylate are obtained, melting at 226° to 230° C.

Analysis for $C_{22}H_{29}N_3OJ_2$: calculated: $C=43.66\%$; $H=4.83\%$; $N=6.94\%$; found: $C=43.18\%$; $H=4.66\%$; $N=7.02\%$.

PREPARATION OF THE STARTING MATERIAL OF THE FORMULA (IV) THROUGH COMPOUNDS OF THE FORMULA (VI)

EXAMPLE 23

To a solution of 2.18 g. of 3-phenyl-4-(2,3-epoxipropyl-$\Delta^2$-1,2,4-oxadiazolin-5-one in 50 ml. of absolute ethanol 1.33 g. of 1,2,3,4-tetrahydro-isoquinoline are added. The reaction mixture is refluxed for two hours. The solvent is evaporated and the residue is dissolved in isopropanol. The solution is acidified with hydrochloric acid in ethyl acetate. 2.47 g. of 3-phenyl-4-[3-(1,2,3,4-tetrahydro-2-isoquinolyl)-2-hydroxypropyl]-$\Delta^2$-1,2,4-oxadiazolin-5-one hydrochloride are obtained in a crystalline form, melting at 210° to 212° C.

Analysis for $C_{20}H_{22}ClN_3O_3$: calculated: C=61.93%; H=5.72%; N=10.83%; found: C=61.62%; H=5.50%; N=11.06%.

EXAMPLE 24

Following the procedure described in Example 23 but starting from 3-(4-chlorophenyl)-4-(3-chloro-2-hydroxypropyl)-$\Delta^2$-1,2,4-oxadiazolin-5-one and 1,2,3,4-tetrahydro-isoquinoline, 3-(4-chlorophenyl)-4-[3-(1,2,3,4-tetrahydro-2-isoquinolyl-2-hydroxypropyl)-$\Delta^2$-1,2,4-oxadiazolin-5-one hydrochloride is obtained, melting at 219° to 221° C., after recrystallization from isopropanol.

Analysis for $C_{20}H_{21}Cl_2N_3O_3$: calculated: C=56.88%; H=5.01%; N=9.95%; Cl=16.79%; found: C=56.65%; H=4.86%; N=10.20%; Cl=16.68%.

EXAMPLE 25

Following the procedure described in Example 23 but starting from 3-benzyl-4-(3-chloro-2-hydroxypropyl)-$\Delta^2$-1,2,4-oxadiazolin-5-one and 1,2,3,4-tetrahydro-isoquinoline, 3-benzyl-4-[3-(1,2,3,4-tetrahydro-2-isoquinolyl)-2-hydroxypropyl]-$\Delta^2$-1,2,4-oxadiazolin-5-one hydrochloride is obtained, melting at 194° to 197° C., after recrystallization from a 96% ethanol.

Analysis for $C_{21}H_{24}ClN_3O_3$: calculated: C=62.76%; H=6.02%; N=10.46%; Cl=8.82%; found: C=63.18%; H=6.13%; N=10.18%; Cl=8.75%.

EXAMPLE 26

40.0 g. of 3-phenyl-4-[3-(1,2,3,4-tetrahydro-2-isoquinolyl)-2-hydroxypropyl]-$\Delta^2$-1,2,4-oxadiazolin-5-one hydrochloride are dissolved in 300 ml. of chloroform, and to the solution 100 ml. of thionyl chloride are added dropwise, under boiling, with stirring. The reaction mixture is boiled for an additional one and a half hours, evaporated on a water bath and the residue is recrystallized from 200 ml. of 96% ethanol. 27.3 g. of 3-phenyl-4-[3-(1,2,3,4-tetrahydro-2-isoquinolyl)-2-chloropropyl]-$\Delta^2$-1,2,4-oxadiazolin-5-one hydrochloride are obtained, melting at 210° to 212° C.

Analysis for $C_{20}H_{21}Cl_2N_3O_2$: calculated: C=59.12%; H=5.11%; N=10.34%; Cl=17.54%; found: C=59.20%; H=5.19%; N=9.99%; Cl=17.88%.

EXAMPLE 27

100.74 g. of 3-phenyl-4-[3-(1,2,3,4-tetrahydro-2-isoquinolyl)-2-hydroxypropyl]-$\Delta^2$-1,2,4-oxadiazolin-5-one hydrochloride are boiled with 126.0 ml. of phosphorus oxychloride for one hour. The solution is evaporated to dryness, to the oily residue 200 ml. of absolute ethanol are added under cooling, the crystalline precipitate is filtered off and finally is washed with ethanol. 84.97% g. of 3-phenyl-4-[3-(1,2,3,4-tetrahydro-2-isoquinolyl)-2-chloropropyl]-$\Delta^2$-1,2,4-oxadiazolin-5-one hydrochloride are obtained, having the same properties as the product obtained in Example 26. Melting point: 210° to 212° C.

EXAMPLE 28

3.8 g. of 3-(2-chlorophenyl)-4-[3-(1,2,3,4-tetrahydro-2-isoquinolyl)-2-hydroxypropyl]-$\Delta^2$-1,2,4-oxadiazolin-5-one hydrochloride and 10.0 ml. of phosphoric oxychloride are boiled for one hour. The mixture is then evaporated and the oily residue is recrystallized from 25 ml. of isopropanol (decoloring). 2.13 g. of 3-(2-chlorophenyl)-4-[3-(1,2,3,4-tetrahydro-2-isoquinolyl)-2-chloropropyl]-$\Delta^2$-1,2,4-oxadiazolin-5-one hydrochloride are obtained.

Analysis for $C_{20}H_{20}Cl_3N_3O_2$: calculated: C=54.50%; H=4.57%; N=9.53%; Cl=24.14%; found: C=54.20%; H=4.84%; N=9.02%; Cl=24.01%.

EXAMPLE 29

10.0 g. of 3-benzyl-4-[3-(1,2,3,4-tetrahydro-2-isoquinolyl)-2-hydroxypropyl]-$\Delta^2$-1,2,4,oxadiazolin-5-one hydrochloride are boiled in a mixture of 70.0 ml. of chloroform and 25.0 ml. of thionyl chloride for 2 hours. The mixture is evaporated and the residue is recrystallized from 96% ethanol. 5.0 g. of 3-benzyl-4-[3-(1,2,3,4-tetrahydro-2-isoquinolyl)-2-chloropropyl]-$\Delta^2$-1,2,4-oxadiazolin-5-one hydrochloride are obtained, melting at 203° to 205° C.

Analysis for $C_{21}H_{23}Cl_2N_3O_2$: calculated: C=16.90%; found: C=16.79%.

EXAMPLE 30

Tablets containing 25 mg. of active ingredient

| | |
|---|---|
| 3-phenyl-6-(1,2,3,4-tetrahydro-2-isoquinolyl)-methyl-4H-5,6-dihydro-1,2,4-oxadiazin dihydrochloride | 25 mg. |
| starch | 80 mg. |
| silica gel | 22 mg. |
| magnesium stearate | 3 mg. |

EXAMPLE 31

Capsules containing 25 mg. of active ingredient

| | |
|---|---|
| 3-phenyl-6-(1,2,3,4-tetrahydro-2-isuquinolyl)-methyl-4H-5,6-dihydro-1,2,4-oxadiazin dihydrochloride | 25 mg. |
| milk sugar | 40 mg. |
| filler | 5 mg. |

The active ingredient content of the pharmaceutical compositions may vary within a wide range.

The daily dose depends on the severity of the patient's condition, on the age, weight of the patient, on the formulation employed and on the activity of the active ingredient, and can also vary within a wide range. The daily dose generally is 1 to 500 mg. active ingredient/kg. of body weight. The above data are for orientation only and deviations in both directions are allowed.

We claim:

1. A compound of the formula (I)

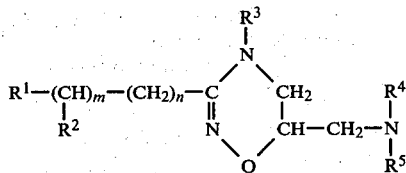

wherein
- $R^1$ is hydrogen or phenyl optionally substituted by one or more of the following substituents: alkyl having 1 to 4 carbon atoms, halogen, alkoxy having 1 to 4 carbon atoms or nitro;
- $R^2$ is alkyl having 1 to 4 carbon atoms, cycloalkyl having 5 to 7 carbon atoms or phenyl, optionally substituted with one or more of the following groups: alkyl having 1 to 4 carbon atoms, halogen, alkoxy having 1 to 4 carbon atoms or nitro; or $R^2$ is naphthyl group;
- $R^3$ is alkyl having 1 to 4 carbon atoms, alkanoyl having 1 to 4 carbon atoms, tosyl or benzoyl which may be optionally substituted by alkyl having 1 to 4 carbon atoms, nitro or halogen, or hydrogen;
- $R^4$ is hydrogen or alkyl having 1 to 4 carbon atoms;
- $R^5$ is cycloalkyl having 5 to 7 carbon atoms, alkyl having 1 to 6 carbon atoms, phenyl-($C_{1-4}$-alkyl) in which the phenyl moiety may optionally be substituted with alkoxy having 1 to 4 carbon atoms, halogen or nitro; or
- $R^4$ and $R^5$ together represent a group of the formula (V)

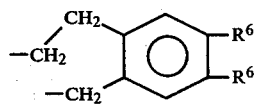

wherein
$R^6$ is hydrogen or alkoxy having 1 to 4 carbon atoms, m and n are each 0, 1 or 3, or a pharmaceutically acceptable acid-addition or quaternary salt thereof.

2. 3-Phenyl-6-(1,2,3,4-tetrahydro-2-isoquinolyl)-methyl-5,6-dihydro-4H-1,2,4-oxadiazine or a pharmaceutically acceptable acid-addition or quaternary salt thereof as defined in claim 1.

3. 3-Phenyl-6-cyclohexylaminomethyl-5,6-dihydro-4H-1,2,4-oxadiazine or a pharmaceutically acceptable acid-addition or quaternary salt thereof as defined in claim 1.

4. 3-Phenyl-6-(6,7-dimethoxy-1,2,3,4-tetrahydro-2-isoquinolyl)-methyl-5,6-dihydro-4H-1,2,4-oxadiazine or a pharmaceutically acceptable acid-addition or quaternary salt thereof as defined in claim 1.

5. 3-(4-Tolyl)-6-(1,2,3,4-tetrahydro-2-isoquinolyl)-methyl-5,6-dihydro-4H-1,2,4-oxadiazine or a pharmaceutically acceptable acid-addition or quaternary salt thereof as defined in claim 1.

6. 3-(2,2-Diphenylethyl)-6-cyclohexylaminomethyl-5,6-dihydro-4H-1,2,4-oxadiazine or a pharmaceutically acceptable acid-addition or quaternary salt thereof as defined in claim 1.

7. 3-(2,2-Diphenylethyl)-6-(N-methyl-N-cyclohexyl)-methyl-5,6-dihydro-4H-1,2,4-oxadiazine or a pharmaceutically acceptable acid-addition or quaternary salt thereof as defined in claim 1.

8. 3-(2,2-Diphenylethyl)-6-(1,2,3,4-tetrahydro-2-isoquinolyl)-methyl-5,6-dihydro-4H-1,2,4-oxadiazine or a pharmaceutically acceptable acid-addition or quaternary salt thereof as defined in claim 1.

9. A pharmaceutical composition containing an amount effective for treating hypertension of at least one compound of the formula (I) as defined in claim 1, or a pharmaceutically acceptable acid-addition or quaternary salt thereof, in association with at least one conventional carrier.

10. A process for the preparation of a compound of the formula (I)

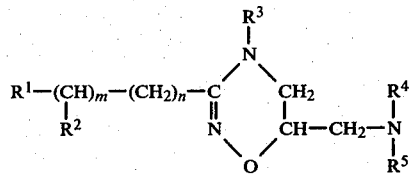

wherein
- $R^1$ is hydrogen or phenyl optionally substituted by one or more of the following substituents: alkyl having 1 to 4 carbon atoms, halogen, alkoxy having 1 to 4 carbon atoms or nitro;
- $R^2$ is alkyl having 1 to 4 carbon atoms, cycloalkyl having 5 to 7 carbon atoms or phenyl, optionally substituted with one or more of the following groups: alkyl having 1 to 4 carbon atoms, halogen alkoxy having 1 to 4 carbon atoms or nitro; or $R^2$ is a naphthyl group;
- $R^3$ is alkyl having 1 to 4 carbon atoms, acyl or hydrogen;
- $R^4$ is hydrogen or alkyl having 1 to 4 carbon atoms;
- $R^5$ is cycloalkyl having 5 to 7 carbon atoms, alkyl having 1 to 6 carbon atoms, phenyl-($C_{1-4}$-alkyl) in which the phenyl moiety may optionally be substituted with alkoxy having 1 to 4 carbon atoms, halogen or nitro; or
- $R^4$ and $R^5$ together are a group of the formula (V)

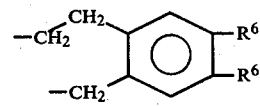

wherein
$R^6$ is hydrogen or alkoxy having 1 to 4 carbon atoms, m and n are each 0, 1 or 2 or a pharmaceutically acceptable acid-addition or quaternary salt thereof, which comprises (a) reacting a compound of the formula (II)

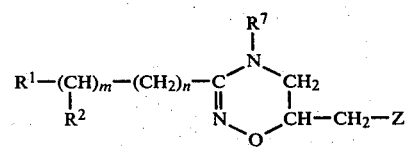

wherein
$R^7$ is hydrogen or alkyl having 1 to 4 carbon atoms, Z is halogen or sulfonyloxy, with a compound of the formula (III)

to prepare compounds of the formula (I), in which
R$^3$ is identical with an R$^7$ group, wherein
R$^7$ is hydrogen or alkyl having 1 to 4 carbon atoms;
or
(b) reacting a compound of the formula (IV)

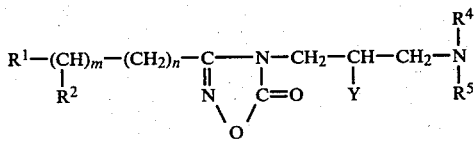

wherein Y is halogen, with a base, to prepare a compound of the formula (I), in which R$^3$ is hydrogen; or
(c) acylating a compound of the formula (I), in which R$^3$ is hydrogen, in a manner known per se, to prepare a compound of the formula (I), in which R$^3$ is acyl; or
(d) hydrolyzing a compound of the formula (I), in which R$^3$ is acyl, in a manner known per se, to prepare a compound of the formula (I), in which R$^3$ is hydrogen, and optionally converting a compound of the formula (I) obtained into a pharmaceutically acceptable acid-addition or quaternary salt thereof.

11. A process as claimed in claim 10, process variant (a) which comprises carrying out the reaction in the melt or in an organic solvent.

12. A process as claimed in claim 10, process variant (a), which comprises carrying out the reaction at the boiling temperature of the solvent employed.

13. A process as claimed in claim 10, process variant (a), which comprises using an equivalent or excess amount of the amine component and/or alkali hydroxide or alkali carbonate.

14. A process as claimed in claim 10, process variant (b), which comprises carrying out the reaction with alkali hydroxides.

15. A process as claimed in claim 10, process variant (b), which comprises carrying out the reaction in water or in a mixture or water and water-miscible organic solvents.

16. A process as claimed in claim 10 which comprises preparing a compound of the formula (I), in which R$^1$, R$^2$ and R$^3$ are hydrogen, R$^4$ and R$^5$ together form a group of the formula (V), in which R$^6$ is hydrogen, and m and n are each O, by starting from the appropriate starting materials.

17. A compound of the formula (IV), in which R$^1$, R$^2$, R$^4$, R$^5$, Y, m and n are as defined in claim 1.

18. 3-Phenyl-4-[3-(1,2,3,4-tetrahydro-2-isoquinolyl)-2-chloropropyl]-Δ$^2$-1,2,4-oxadiazolin-5-one.

19. A method of treating hypertension in an animal which comprises the step of administering to said animal an effective amount of the compound defined in claim 1 or a pharmaceutically acceptable acid-addition or quaternary ammonium salt thereof.

* * * * *